(12) United States Patent
Egea Bermejo et al.

(10) Patent No.: US 10,357,526 B2
(45) Date of Patent: Jul. 23, 2019

(54) **COMPOSITIONS FOR THE TREATMENT OF INFECTIONS CAUSED BY MITE *DEMODEX* SPP**

(71) Applicant: PROCAPS S.A., Barranquilla (CO)

(72) Inventors: Eduardo Egea Bermejo, Barranquilla (CO); Gloria Garavito De Egea, Barranquilla (CO); Raimundo Abello Llanos, Barranquilla (CO); Dary Luz Mendoza Meza, Barranquilla (CO); Martha Lizarazo Carreño, Barranquilla (CO); Luis Escaff Jaraba, Barranquilla (CO); Luis Carlos Escaff Sales, Barranquilla (CO)

(73) Assignee: PROCAPS SA, Barranquilla (CO)

( * ) Notice: Subject to any disclaimer, the term of this patent is extended or adjusted under 35 U.S.C. 154(b) by 0 days.

(21) Appl. No.: 15/647,201

(22) PCT Filed: Dec. 30, 2014

(86) PCT No.: PCT/IB2014/067414
§ 371 (c)(1),
(2) Date: Jul. 11, 2017

(87) PCT Pub. No.: WO2016/108070
PCT Pub. Date: Jul. 7, 2016

(65) Prior Publication Data
US 2018/0353560 A1 Dec. 13, 2018

(51) Int. Cl.
*A61K 36/906* (2006.01)
*A61K 36/31* (2006.01)
*A61K 36/9062* (2006.01)
*A61K 36/9068* (2006.01)
*A61K 9/00* (2006.01)
*A61K 47/14* (2017.01)
*A61K 47/44* (2017.01)

(52) U.S. Cl.
CPC ............ *A61K 36/31* (2013.01); *A61K 9/0014* (2013.01); *A61K 36/9062* (2013.01); *A61K 36/9068* (2013.01); *A61K 47/14* (2013.01); *A61K 47/44* (2013.01)

(58) Field of Classification Search
CPC ..................................................... A61K 36/906
See application file for complete search history.

(56) References Cited

U.S. PATENT DOCUMENTS

| 2005/0048008 A1* | 3/2005 | Gupta | A61K 8/447 424/59 |
| 2005/0058672 A1* | 3/2005 | Gupta | A61K 8/26 424/401 |
| 2005/0215635 A1* | 9/2005 | Rafi | A61K 8/35 514/546 |

\* cited by examiner

*Primary Examiner* — Rosanne Kosson
(74) *Attorney, Agent, or Firm* — Isaac Angres

(57) ABSTRACT

The invention relates to compositions and kits for treating infections caused by the mite *Demodex* Spp, said compositions comprising essential oils selected from the group consisting of *Eruca sativa* oil, *Zingiber officinale* oil, and *Alpinia officinarum* oil and mixtures thereof incorporated into solvents and vehicles, and presented in a kit in the form of a solution, a suspension, an emulsion or a dispersion. The compositions are topically applied for the treatment of infections and disorders caused by *Demodex* Spp in humans.

8 Claims, 1 Drawing Sheet

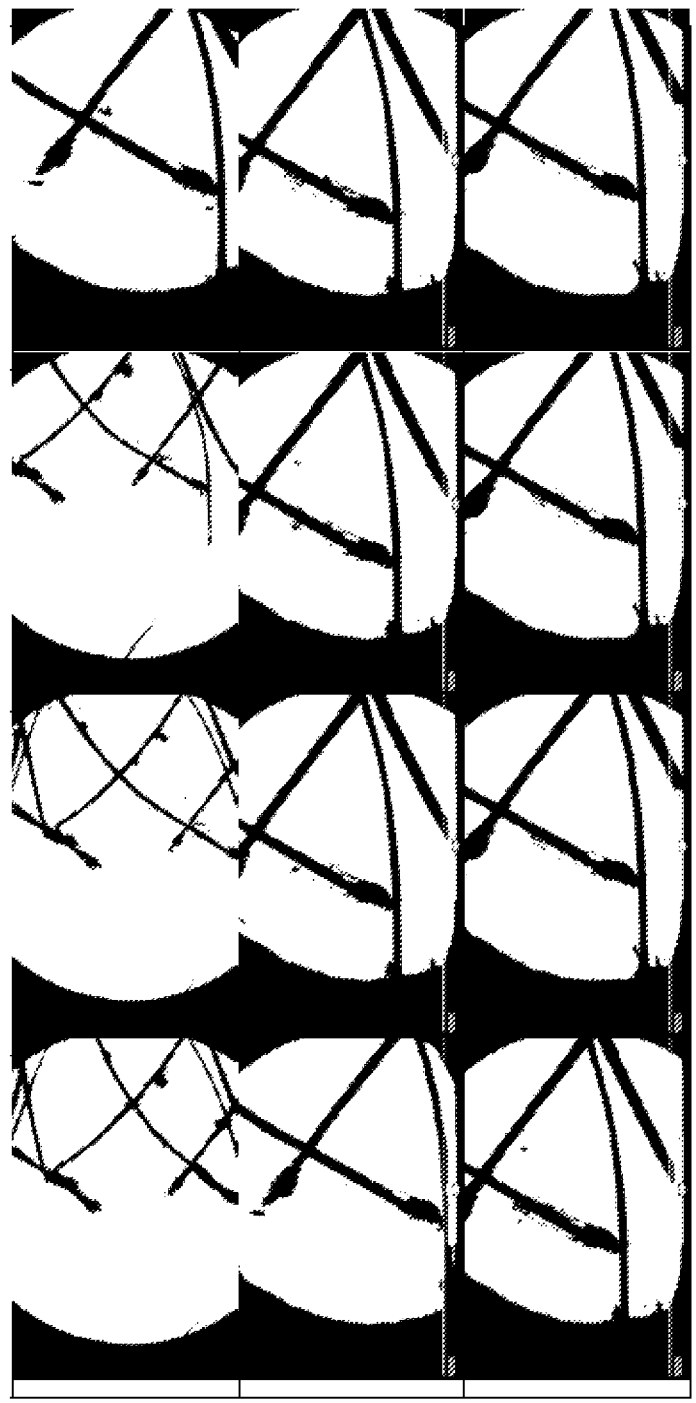

COMPOSITIONS FOR THE TREATMENT OF INFECTIONS CAUSED BY MITE *DEMODEX* SPP

This application is a continuation-in-part of international application No. PCT/IB2014/067414 (published as WO2016/108070) titled "Compositions For Treating Infections Caused By The Mite *Demodex* Spp" filed Dec. 30, 2014; the entire contents of which are hereby incorporated by reference herewith.

OBJECT OF THE INVENTION

The present invention relates to compositions of essential oils for the treatment of infections caused by the *Demodex* Spp mite.

More in particularly, the present invention is directed to a composition for the treatment of ophthalmic infections such as blepharitis and for treatment of people with a condition known as Demodicosis produced by the mite *Demodex* Spp and whose symptoms include eye irritation including dry eyes, itching, decreased vision and madarosis or loss of eyelashes. Other uses of the composition of the present invention, without being limiting, are all diseases caused by the human mite *Demodex* Spp. According to the invention, the acaricidal effect of the composition of the invention is because it dehydrates the mite eggs by lipolytic effect so that it solubilizes the lipid membranes of the anatomical structure of the animal and thus removes it.

FIELD OF THE INVENTION

The present invention describes combinations of essential oils for the control and treatment of ophthalmic infections such as blepharitis and those related to Demodicosis produced by the mite *Demodex* Spp.

The composition of the present invention comprises the single oil or mixture of essential oils obtained from the plants *Zingiber officinale, Alpinia officinarum* and *Eruca sativa mili* having acaricidal and destructive action on *Demodex* Spp mites by topical application in the eyelashes, eyebrows, eyelids and/or surrounding skin, managing to destroy the *Demodex* ssp.

BACKGROUND OF THE INVENTION

Blepharitis is one of the most frequent reasons for ophthalmologic consultation. This condition has been linked to the presence of the mite *Demodex folliculorum*. In the vast majority of cases, this is an ectoparasite guest in humans without causing harm. However, in some individuals, especially those with compromised immune systems, or diseases such as rosacea, *Demodex* population can increase dramatically, resulting in a condition known as demodicosis. At present there are a variety of pharmaceuticals for treating demodicosis, which must be monitored carefully because of the risk of toxicity. Others have limited effectiveness because the mite develops resistance.

*Demodex folliculorum* is a mite that typically resides in the hair follicle, which causes chronic eczematous blepharitis (Ibis Sedeño, Ester Novoa, Vivivan Register, Francisco Garcia and Raul San Martin Salem DA-B, the-shazly A Nabih N, El-Bayoumy Y, Saleh S., Blepharitis by *Demodex* infestation, diagnosis and treatment. Revista Cubana Oftalmol 2006. 19). It has also been associated with other diseases such as rosacea, folliculitis, perioral dermatitis among others (Forton F, Seys B. Density of *Demodex* infestation in rosacea: a case control study using standardized skin surface biopsy, British J Dermatol 1993; 128: 650-59). However, the role of *Demodex* as a causative agent of human disease is still a matter of controversy. These mites are acquired shortly after birth and normalize skin wildlife. Their number is increased in proportion to the available food supply, so that they increase during puberty when the sebaceous glands proliferate. It is very common to find in inflammatory facial lesions, but causality is difficult to prove (Elston D M *Demodex* mites: Facts and Controversies Clinics in Dermatology September 2010; 28 (5): 502-4).

*Demodex* also in addition to man affects a variety of animals such as dog, cat, horse, cow, pig, goat, bat, rat, mouse, rabbit and hamster but differences were found in the *Demodex* species of different animals, e.g. it has been called *Demodex canis* in dogs and *Demodex phyilloides* in pigs (Corridor R, Nava, Tovilla J, Munoz S., Blepharitis *Demodex folliculorum* Rev Fac Med UNAM 43 (4):125-9).

Blepharitis association with the presence of *Demodex* infestation is probably more common than suspected by ophthalmologists. This parasitic mite prefers to reside in hair follicles, sebaceous glands and the eyelashes of man. It is widely distributed worldwide. We have found two types: *Demodex longus* infestation *longus* and *Demodex brevis* infestation.

The *Demodex longus* infestation and *Demodex brevis* infestation are found in about 10% of biopsies of healthy skin, where they are present in about 12% of all hair follicles. Both species are most common on the face. *Demodex brevis* is the predominant mite having a wider distribution in the body. Normal colonization rates are between 20% and 80%. Men often are more affected than women, probably because they have more sebaceous glands, although the opposite was found among Australian *Aborigines* (Norn M S *Demodex* infestation Incidence and possible pathogenic role in the human eyelid. Chapter IV: Incidence in the ocular region of a clinical material Acta Ophthalmol, *Demodex* infestation Suppl 1970; 108: . . . 43-52).

A study of cases and controls assessed the prevalence of infection by *Demodex* infestation in one hundred patients with chronic blepharitis and 100 healthy controls. The prevalence in the group of blepharitis, was 63% compared with the control group only having mites in 33.33% of cases (p<0.001). The analysis adjusted for gender showed that women had the mite in 44.63% and men in 53.85% of cases proving that *Demodex* infestation plays an important role in the pathophysiology of chronic blepharitis (Gamboa J, Cortes M, A. Rodriguez, Incidence of *Demodex* infestation in blepharitis Rev Mex Ophthalmol 2003; 77 (2): 44-7).

A meta-analysis with a solid and comprehensive design was conducted and reviewed the available literature on the association of *Demodex* infestation with blepharitis including eleven articles covering reports from four different countries and 4,741 patients participating (2,098 blepharitis and 2,643 controls. The analysis found a pooled OR of 4.89 with a confidence interval of 95%, 3.00 to 7.97).

Sensitivity analysis showed that the pooled results effects in different models, language, sample size and control groups were completely consistent, demonstrating a stable association between *Demodex* infestation and blepharitis. The authors conclude that when the conventional treatment of blepharitis fails, one should evaluate the possibility of *Demodex* infestation and consider the respective acaricide treatment (Zhao Y E, LP Wu, Hu L, Xu J R Association of blepharitis With *Demodex*, Meta-analysis, Ophthalmic Epidemiol., April 2012; 19 (2): 95-102).

Demodicosis is the term used to describe skin diseases caused by mites of the genus *Demodex folliculorum longus* and *Demodex brevis*. They live as normal microflora in the skin of humans especially in the hair follicle and pilosebaceous complex. This mite was discovered in 1841 in the external auditory meatus. Subsequently, it was described in detail by Simon in 1842, who proposed the term *Demodex* infestation, and *D. folliculorum, D. Fuloculorum* and *D. brevis* (Owen R, 1843—A list of the parasitic Protozoa, Helminths and arthropods recorded from species of the Family Anatidae).

*Demodex* sp are man bound ectoparasites. More frequently they inhabit in high density areas of craniofacial skin, including nose and peri orbital region. It is known that 10% of all biopsies and 12% of all hair follicles present with the human *Demodex* mites. The prevalence of both species increases with age, but the prevalence of *Demodex brevis* is lower. Both species are found in facial demodicosis, which is the site of infection (Norn M S, 1972) were it occurs most often. In the rest of the body, *Demodex brevis* has a broader distribution, causing body demodecosis (Norn M S *Demodex* infestation Incidence and possible pathogenic role in the human, Acta Ophthalmologica Suppl eyelid 1970; 108: 1-85).

Infection by *Demodex* Spp produces in humans keratoconjunctivitis and blepharitis (AE Rodriguez, 2005). It has also been associated with other dermatoses such as rosacea and peri oral dermatitis. Recently, evidence has been found of an association with basal cell carcinoma (Amichai B, 1992; Forton F, 1993; Erbagci Z, Robinson T W E 2003—*Demodex* infestation and Rosacea Arch Dermatol 1965; 92: 542-544).

The biology of *Demodex folliculorum* infestation biology comes from the Greek demos meaning fat; and dex, meaning woodworm (Forton F., 1993). *Demodex* belongs to the arthropod phylum, class Arachnida, order: Acari; superfamily: Demodicodoidea. Based on taxonomic criteria, Martinez-Baez M (1953) it is classified as a species that affect humans, such as *Demodex longus* infestation and *Demodex brevis* (Markell E K, John D T, Krotoski W A Arthropods and Human Disease In. WB Saunders Company, editors. Markell and Voge's Medical Parasitology. Philadelphia, 1999, p. 361.).

The life cycle of *Demodex folliculorum* infestation occurs in the opening of the hair follicle host. The female makes its way into the sebaceous gland into which it lays eggs about 12 hours, the larvae then hatches 60 hours after ovoposition. The larvae is fed and continuously moving and after a life of approximately 40 hours, gives rise to the protonymph. This occurs in the pilosebaceous duct. The protonymph eats continuously and is simultaneously transported to the follicle opening in the pilosebaceus duct. The legs of the protonymph compared to the adult are weakly developed, for this reason offers little resistance. The protonymph after a 72 hour life gives rise to deutonymph. After a short time interval during which the deutonymph inches towards the skin surface, it can be in a period after 36 hours, but usually remains about 12 hours and probably only in the dark or partial light. The deutonymph then enters the follicle and after a life of 60 hours moves on to become an adult. The female remains in the mouth of the follicle until the time of copulation. Adult female moves from inside the mouth of the follicle, after oviposition, where after a life of approximately 120 hours they die (Desch C E, 1977).

It has been shown that about half of the mites at the mouth of the follicle are dead. Dead mites tend to block the follicular opening, which would tend to reduce the opportunity for new infestations of individual follicles. A rough estimate of the evolutionary cycle of the female would be: 60 hours egg, larva 36 hours, protonymph 72 hours, 60 hours deutonymph, adult female 120 hours for a total of 348 hours or 14 and a half days. This has been evidenced in vitro culture (Acaricide Blepharitis by *Demodex folliculorum* Biomicroscopic findings, Arch Ophthalmol Soc Españ 1993; 65: 455-462).

It has been experimentally shown that *Demodex* at all stages flees the light (negative phototaxis). Larva, and adult female protonymph migrate into the wider portion of the follicle, while the adult male and deutonymph can move towards the narrower part thereof. The deutonymph is more resistant to heat and desiccation at the other stages (Humiczewska M., *Demodex folliculorum* and *Demodex brevis* Acarides as the factors of marginal chronic blepharitis, Wiad Parazytol 1991; 37 (1): 127-30).

Regarding habitat, although the *Demodex longus* infestation and *Demodex brevis* have been found in the skin pilosebaceus complex, they occupy different sites. *Demodex longus* infestation level inhabits the sebaceous glands or pilosebaceous ducts (Forton F et al. 1993 and Duke-Elder S 1974). Meanwhile, *Demodex brevis* inhabits sebaceous and meibomian glands. *Demodex longus* infestation consumes cells of the follicular epithelium, however epithelial metaplasia and follicular distension can occur only if there are 6 or more mites present in the same follicle, therefore it is considered a low grade pathogen.

*Demodex brevis* apparently consumes sebaceous glands, but there is no evidence of metaplasia (Uyttebroeck W, Nijs I, Maudgal P C, Missotten L., Incidence of *Demodex folliculorum* on the eyelash follicle in normal people and in blepharitis patients, Bull. Soc. Belge. Ophtalmol, 1982; 83-7).

*Demodex* has been implicated as the agent associated with persistent dry skin, erythematous scaly rosacea resembling *pityriasis*, the papulopustular or the granulomatous rosacea (Amichai B, 1992), including location in isolated inflammatory papules, alopecic scalp and in some cases blepharitis, seborrhea, skin atrophy, palpebral skin pigmentation, and meibomitis chalazia. It has also been associated in immunosuppressed patients with leukemia or HIV infection and cancer chemotherapy (liva J, 2010—Morras P G, Santos S P, Imedio I L, Echeverria M L, Hermosa J M., Rosacea-like Demodicidosis in an immunocompromised child Pediatr Dermatol., 2003; 20: 28-30).

*Demodex brevis* is a more solitary species than *Demodex folliculorum longus*. Usually a single mite lives or at most two, presumably a female. (Desch C E., 1972). Usually a single species is found although the two species together may also be found. It has been shown that the most common place is on the nose, then the external auditory meatus and eyelashes (Duke-Elder S. 1974), and it can also be found on the cheek. *Demodex* is more abundant in the lower eyelid than at the top, which can be explained by the shortest migration path from the nose. The severity of the infection may play a role in migration to the eyelashes, and searching for other niches where they can play and have enough food (Norn M S Incidence of *Demodex* infestation on skin of lids and donot ophthalmologica Act 1982; 60: 575-583).

In related studies, it was found that an adult *Demodex* walks about 7 to 8 mm in 30 minutes. Duke-Elder and Dubois (1974) found no mites in children under 5 years, but did find mites in 50% of children aged between 5 and 10 years and universally in individuals aged over 25 years old (Coston 1987). Norn M S (1982) found mites in virtually all middle-aged subjects (7 years). Post and Juhlin E (1965), found 59% prevalence by *Demodex* species. Madeira and Sogava (1993) reported 72% of patients infected by *Demodex*, of which 51% have *Demodex folliculorum longus* infestation, 2% *Demodex brevis* and 19% both species.

Aylesworth R & Vance J C (1982) studied these mites in a consecutive series of skin biopsies submitted to a Dermatopathology laboratory, finding that 12% of all follicles contain *Demodex* mites. The prevalence of both species increases with age, but the prevalence of *Demodex brevis* was always lower. Although the face skin is more heavily infested by both species, *Demodex brevis* has a wider distribution in the body. Men are infected more than women with both species.

Meral Turk et al. (2007) noted that the incidence of *Demodex folliculorum* infestation was higher in patients with blepharitis compared to normal controls. Comparative studies of demodicosis in humans and other mammals indicate that keratinization, hyperplasia, bloating, and aggregation of melanocytes can be even wider if populations of *Demodex folliculorum* infestation accumulate in the follicles of the eyelids. Large populations of *Demodex brevis* can destroy the glandular cells, producing granuloma on the eyelid and plug conduits or meibomian sebaceous glands. Further studies may implicate one or both species with microorganisms, transfer agents or synergists, or both, in the production of ocular disease in man (Madeira N G, Sogava M I. Prevalence of *Demodex folliculorum* infestation and *Demodex brevis* A sample of the population of Botucatu, Sao Paolo Trop. Med. Rev. Bras. Soc., 1993; 26 (4): 221-224).

Ayres S (1967) and Georgala S (2001), assessed the significance of *Demodex folliculorum longus* infestation in the etiology and course of rosacea, concluding that although *Demodex* mites do not appear to be the cause of rosacea, they can represent an important cofactor especially in papula-pustular rosacea. Immunohistochemical findings suggest that a delayed hypersensitivity reaction, possibly triggered by antigens of follicular origin, probably related to *Demodex longus* infestation, can occur, encouraging the progression of the condition to papulopustular stage. Recently results of the presence of *Bacillus oleronius* in *Demodex* mites within a patient papule-pustular rosacea were published. It was found that this bacterium produces antigens capable of stimulating proliferation of mononuclear cells in peripheral blood in 73% of rosacea patients compared with control subjects (p=0.0105). In addition, a pool of sera from 6 patients with papule pustular rosacea identified two proinflammatory proteins of 62 kDa and 83 kDa-produced by this bacterium (N Lacey et al., 2007). Further studies revealed the existence of a statistically significant correlation between serum immunoreactivity antigens *Bacillus oleronius, Demodex* sp., and facial rosacea. A total of 59 registered patients prospectively and consecutively, a significant positive correlation between serum immunoreactivity with facial rosacea (p=0.009) and ocular *Demodex* infection (p=0.048) was found. Facial rosacea patients had significantly higher *Demodex* infection compared to those without rosacea (p=0.014) (Jianjing L i, 2010). Although it is still speculative, existence of a causal relationship between serum immunoreactivity, ocular infection by *Demodex* and rosacea, there is speculation of a new paradigm that links pathogens such as *Demodex* and microbial infection by *B. Oleronius* with inflammation on the ocular surface. The co-morbidity of both microorganism *Demodex* mites and *B. Oleronius* is based on symbiosis of the latter in the mite (Kuhnigk T. 1995; Jianjing L i, 2010—Robinson T W E *Demodex* infestation and Rosacea Arch. Dermatol 1965; 92: 542-544.).

Treatment of Demodicidosis is currently aimed at eliminating the parasite. One of the traditional methods is to expose the tails of the mites outside the hair follicle, by cleaning palpable borders and edges with ether, followed by observation of the mites with a slit lamp and then application of selenium disulphide 0.5% alone or in combination with hydrocortisone acetate 0.5% based petrolatum or benzyl benzoate (runner-Osorio, 2000; Norn M S, 1982). There is also used as treatments ointments based on ammoniated mercury (1 to 3%) and yellow mercuric oxide, although this treatment has limited duration of six weeks under common control, due to the corneal toxicity of mercury. Other treatments include antimicrobial topical metronidazole 2%, permethrin 1%, lindane 1%, crotamiton 10% (Forton F, 1993; Junk A K, 1998) and erythromycin, however it is now known that the mites have developed resistance to these treatments. Alcohol is also used at 10% concentration, povidone-iodine and also the use of Ivermetrin (Aquilina C, 2002).

Other treatments include the use of essential oils. In vitro studies have shown that the essential oil extracted from Tea Tree, has the property of rapidly eliminating the *Demodex* mite (messager S, 2005; Gao Y Y, 2005). The tea tree oil is extracted from the leaves of the tree *Melalua alternifolia* (Myrtaceae), which is native to eastern Australia. The oil showed acaricidal activity against *Demodex* in a short time of 4 minutes, but has the disadvantage of being toxic. In a recent study, in vivo use of Tea tree oil as a 50% solution with fixed oil of the Macadamia nut *ternifolia* (Proteaceae), as a treatment to eliminate *Demodex* mites living in the flanges of the patients reported afflicted with ocular rosacea, demonstrated improved conjunctival irritation and inflammation at six weeks of treatment (Y Y Gao, 2005; Gao Y Y, 2007).

Wen-ge Li (2005) showed acaricidal activity against *Demodex* with five creams made from volatile oils of *Curcuma longa* (Zingiberaceae), *Syzygium aromaticum* (Myrtaceae), *Eucalyptus globulus* (Myrtaceae), *Zingiber coralliaum* (Zingiberaceae) and *Litsea pungens Hemsl* (Laureceae); finding a maximum acaricidal activity with a cream made with oil *Curcuma longa*. Subsequently, Zhao Yae et al (2006) demonstrated the effectiveness of *eucalyptus* tree oil against *Demodex* infestation. Song Bo et al (2010), evaluated the effect in vitro of the acaricide *Gengibre* pure blue (Zingiberaceae) essential oil, finding that this was able to eliminate *Demodex folliculorum* mites in 14.42-1.14 minutes of treatment and, *Demodex brevis* in 8.3 to 0.86 minutes of treatment. All these products have an irritant and toxic long-term effect.

At present there are a variety of pharmaceuticals for treating demodecosis, which must be used carefully because of the risk of toxicity. Others have limited effectiveness because the mite develops resistance.

The mite *Demodex folliculorum*, was discovered by Henle and Berguer in 1841 and described in detail by Simon in 1842 and has since then been the subject of study. It is a mite of the Demodicidae family, often called "follicle mite" because it lives inside the hair follicles of their hosts. It is vermiform, has four pairs of stubby legs and a striatum abdomen, lives in the sebaceous glands of the head, hair follicles of the face, eyelashes and meibomian glands of the eyelids, but can also be found in the chest, armpits and pubic region. Although found in asymptomatic individuals, their presence has been linked with various ophthalmological diseases such as conjunctivitis, chronic eczematous blefaritis, chalazia and contact lens intolerance. Its incidence in men increases with age.

The prior art reveals some treatments against *Demodex* Spp. Essential oils are more or less volatile substances, characterized by a strong odor and can contain about 20 to 60 components in very different concentrations, produced either by steam distillation or dry distillation or by a mechanical treatment of one species. These derived volatile compounds are mainly terpenes and their oxygenated derivatives, cyclic hydrocarbons, alcohols and aldehydes. Among the most important methods of obtaining essential oils in the prior art are the steam stripping; cold press extraction; solvent extraction by supercritical fluid extraction; hydrodistillation extraction assisted by microwave radiation; and effecting pretreatment with ultra low frequency sound.

An example of the use of essential oils having acaricidal effects, is one derived from the tea tree, such as disclosed in United States published patent application No. US 2012/0004320, to Gao, Yingying and others, and relating to a method for treating ocular disorders caused by the mite *Demodex*, such as blepharitis, *Demodex* induced rosacea, acne, etc., which method comprises administering to the patient a composition comprising a therapeutically effective amount of an oil chosen from a isoprenoidal essential oil substance such as tea tree oil; Terpinen-4-ol; carvone; alpha-terpineol; Cardinene; d-carvone; 1-carvone; gamma-terpinene; alpha-terpinene; 1, 8 cineole; alpha-terpineol; para-Cimene; alpha pinene; Limonene; (R)-(+)-Limonene; alpha-Thugene; eucalyptol; (+)-Ledene; Cuminic aldehyde; and Myrcene; where the administration comprises contacting the affected area of the lid margin and the tabs of the patient with the composition. However, it has been found that this composition based on tea tree is not completely effective because it does not act on the deformation of the animal body therefore its removal is not guaranteed.

All developments by Gao, are directed to treatment by using tea tree oils and therefore its consequent elimination is not fully guaranteed. For example patent applications in the US, such as US20090061025 to Gao et al discloses compositions containing about 0.6% to 20% tea tree oil in the form of solutions, suspensions, aerosols, lotions, gels, pastes, impregnated wipes, impregnated tissue, impregnated non-woven substrates, balms medicinal, cleaning products (including shampoos and soaps), creams or ointments. According to Gao et al, their invention is directed to compositions and methods for use in treating ocular infestations caused by *Demodex* Spp and related diseases using such compositions. According to US patent application US20130344128 also to Gao et al, a method is disclosed for treating an eye disorder such as blepharitis induced by the mite *Demodex* Spp, also treating rosacea, acne and dysfunction of the meibomian glands in a patient in need thereof, which method comprises administering to the patient a composition comprising a therapeutically effective amount of an essential oil chosen from the tea tree.

Gao also discloses the miticidal effect that occurs only at certain concentrations, but also illustrates the adverse irritation effects that occur in humans ranging from burns to tissue necrosis. Indeed, according to the studies reported by Gao, Yingying and others such as the background patents discussed above and in the publication entitled "In vitro and in vivo killing of ocular *Demodex* by tea tree oil (Destruction in vitro and in vivo of *Demodex* in the eye using tea tree oil), Extended Report Br. J. Ophthalmol 2005; 89: 1468-1473 doi: 10.1136/bjo Jun. 6, 2005; defined concentrations that generated varying degrees of irritation in some patients.

Another example of prior art is Patent Application US20040156873 to Gupta et al disclosing compositions for treating acne and rosacea with a treatment strategy using a synergistic combination for controlling the production of excess sebum; control of undesirable bacteria or mites; control inflammation; increasing the peeling of follicular infundibulum cells; reducing anti-acne rosacea or irritation; and improved bioavailability of the topical anti-acne and rosacea compositions. This is achieved by a synergistic combination of anti-acne and rosacea topical ingredients, commonly used with a topical composition having improved bioavailability, which results in increased action of anti-acne and rosacea treatment based on the ingredients. Moreover, this prior also discloses the additional inclusion of an anti-inflammatory composition and a composition for improving vascular microcirculation.

U.S. Pat. No. 7,575,764 to Chen et al discloses topical compositions comprising *Hypsizygus ulmarius* extract in amounts that are effective to influence polymorphonuclear leukocytes mediated chemotaxis. *Hypsizygus ulmarius* extract may be used alone or in combination with anti-inflammatory active agents and secondary skin agents, such as other fungi and/or natural extracts. Secondary anti-inflammatory agents may or may not function by antagonizing mediated chemotaxis. According to that patent, the extract can be incorporated into a cosmetically acceptable carrier.

PCT WO0151014 to Eini et al discloses a composition for topical application characterized by rheological properties comprising by weight, 1 to 25% of a solidifying agent and 75-99% of a hydrophobic solvent, wherein the solidifying agent is selected the group consisting of a fatty long chain alcohol having at least 15 carbon atoms in its carbon backbone and a fatty acid having at least 18 carbon atoms in its carbon backbone and wherein said solidification agent includes a substance selected so that under ambient conditions, the carrier is semi-solid at rest and liquefies with the application of shearing thereto and wherein said hydrophobic solvent is selected from the group consisting of at least an oil derived from a marine animal or terrestrial or a mineral oil and at least one vegetable oil.

US application No. 20130053353 to Tamarkin et al, illustrates a substantially surfactant free composition for cosmetic or pharmaceutical application comprising: a) a first rheology modulator comprising a suspended pharmaceutical active agent or a suspended cosmetic active agent; b) a second rheology modulator selected from the group consisting of: at least one fatty alcohol, at least one fatty acid, at least one wax, and mixtures of two or more thereof; and c) a hydrophobic carrier comprising at least one hydrophobic solvent; wherein the composition comprises less than about 0.1% by weight surfactant; wherein the composition comprises less than about 2% by weight water; wherein the viscosity of the composition is at least about 30% higher than the viscosity of a first partial composition comprising the second rheology modulator agent and the hydrophobic carrier without the first rheology modulator; and is higher than the viscosity of a second partial composition comprising the first rheology modulator and the hydrophobic carrier without the second rheology modulator; and wherein the viscosity of the first partial composition is less than about 25,000 cPs at room temperature.

Therefore, there is a long term need for a composition with regard to the form of administration which include therapeutic application easily without causing toxicity, rapid acaricide action and effective action not only in the mite itself but eggs that have been deposited, resulting in greater action in clinical treatment.

So, an important aspect of the instant invention is that the acaricide action does not cause severe and adverse effects in humans and in turn, dehydrate and destroy the mites and their eggs by the lipolytic effect that solubilizes the lipid membranes of the anatomical structure the mites.

BRIEF DESCRIPTION OF THE FIGURES

To further clarify the invention and its advantages compared to the prior art, the invention is described below with the help of the attached FIGURES, and includes possible ways of illustrating nonlimiting embodiments of the principles and application of the invention.

FIG. 1 shows a microscopic 4× photographic sequence observation of the mites in the sample of an in vitro tab from the start of the acaricidal activity assay of the composition of the present invention to after 5 minutes.

SUMMARY OF THE INVENTION

The invention provides an acaricidal a composition for the treatment of infections and diseases caused by *Demodex* Spp mite, which comprises essential oils selected from the group consisting of *Eruca sativa mili* oil, *Zingiber officinale* and *Alpinia officinarum* oil and mixtures thereof.

The invention also provides a kit for the treatment of illnesses in humans by the mite *Demodex* Spp comprising: (A) a composition comprising essential oils selected from the group consisting of *Eruca sativa* oil *mili* oil, *Zingiber officinale* oil and *Alpinia officinarum* oil and mixtures thereof wherein the essential oils are incorporated in an acceptable solvent; forming a pharmaceutical solid, semi-solid or liquid; (B) an insert specifying the use of said composition to the affected area and the frequency of application; and (C) an appropriate container for application of the dosage forms.

DESCRIPTION OF THE INVENTION

The present invention comprises a composition having acaricidal activity (especially anti-mite activity) based on the combination of essential oils obtained from the plants *Eruca sativa mili*, *Alpinia officinarum* and *Zingiber officinale* for topical application that destroys mite eggs and their lipolytic effect which solubilizes the lipid membranes of the anatomical structure of the animal. The individual oils are also usable by themselves.

The present invention resides in the long term need in the art of a composition which relative to the form of administration includes easy therapeutic application without causing toxicity, it has rapid acaricide action and effective action not only against the mite itself but the eggs deposited, resulting in greater activity in the clinical treatment setting.

For this long term need purpose, based on the background art for the present invention the acaricidal effect of various types of plant oils, including the prior reference essential oil or tea tree of Maleleuca was evaluated.

For the present invention, a comparative study and analysis was conducted which studied the acaricidal activity and characteristics of essential oils used in pure and undiluted form, from plants such as *Eruca sativa mili*, the *Alpinia officinarum*, *Zingiber officinale*, the Tea Tree, galanga and Black Pepper whose results are evident and reported in the comparison table 1 below.

TABLE NO. 1

Results of the acaricidal activity of the pure essential oils. Descriptive Statistics

| Essential pure Oil | Average life time in minutes of Acaro (mites) | Standard deviation | N |
|---|---|---|---|
| Galanga | 10.22 | 1.26458 | 10 |
| Zingiber officinale | 11.45 | 1.17059 | 10 |
| Tea tree | 3.6327 | 0.43713 | 11 |
| Black Pepper | 30.049 | 8.85451 | 10 |
| Eruca sativa mili seeds | 9.794 | 1.18796 | 10 |
| Alpinia officinarum | 4.853 | 1.11517 | 10 |

N: number of mites tested in the oils.

As evidenced and described in Table 1, it is seen that the pepper and Galanga had lower acaricide activity. The Maleleuca or tea tree was the product that was taken as a reference based on the prior art, where it was found to have acaricidal effect at certain concentrations but having adverse effects, causing severe effects in humans ranging from burns to tissue necrosis as evidenced in some patients according to the studies reported by Gao.

Therefore, for the composition of the present invention, the essential oils of *Eruca sativa mili*, *Alpinia officinarum* and *Zingiber officinale* were selected for the novel compositions of the invention.

For its part, the *Eruca sativa mili* includes names such as Arugula, Arugula or Jazamango and belongs to the family of Brassicaceaes and gender of *Eruca*. This plant is native to the Mediterranean and western Asia and the uses of this plant are mostly for consumption of leaves and young stems, which are eaten raw in salads and Mediterranean diets. It is also considered as a medicinal plant and can be used in biological pest control.

Next, the plant *Zingiber officinale*, belongs to the family of Zingiberaceaes and gender of *Alpinia*. The *Zingiber officinale* is a plant that is distributed in the Himalayan region and South Western Ghats region in India. It is a plant used in cooking as food, especially Thai and Indonesian cuisine. It is one of the four plants known as galangal and differs from the others in being the largest. It is also used in diets for poor appetite, hypersecretory dyspepsia, flatulence, asthenia and convalescence. Popularly, it is also used in dysmenorrhea, prevention of vomiting and dizziness and chewed to help relieve toothaches. It is also used as digestive aids, anti-spasmodic, anti-inflammatory, carminative, anti-emetic and general well being.

Finally, the *Alpinia officinarum* is a plant of the family of gingers, *Alpinia* gender. The *Alpinia officinarum* comes from Asian countries, especially China, and is commonly known as lesser Chinese galanga, *Alpinia officinarum* whose underground stem is a horizontal rhizome prized for its aroma and spicy flavor. The plant grows to have 90 cm in length, with 20 cm long leaves.

For the present invention, an experimental design for acaricidal evaluation of essential oils of the plants *Zingiber officinale*, *Eruca sativa* and *Alpinia officinarum mili* was chosen. An experimental evaluation scheme was used to evaluate the acaricidal effect of each of the oils both individually and in combinations thereof using field microscopy. The experiments were carried out on mites individually and in between one and the others. The experiments were repeated more than 50 times and the clustering of mite was evaluated by field microscopy and always in fields that showed a number of mites greater than 5 per microscopic field. According to the results obtained, the present invention comprises a mixture represented by the concentrations of the three oils mentioned above as being most effective in their acaricidal action to demonstrate their effect on the *Demodex* Spp.

For the purpose of the invention, the evaluation of the acaricidal activity of the mixture was done on more than 30 microscopic fields, showing the acaricidal effect, as evidenced in the tables defined below and accompanied by the descriptive statistics on each one. These studies were carried out by the inventors in the Laboratory of Immunology and Molecular Biology of the University of the North in Barranquilla, Colombia.

According to studies of the compositions of the present invention, assays were performed in real time about the total number of mites that were present under the same observation field. The minimum number of mites per field was five and the average number of mites was always equal to or greater than five.

Before evaluating the miticide effect of each of the oils, miscibility and safety thereof on mites was studied. Tables 2 and 3 show the results of those tests.

TABLE NO. 2

Evaluation of the solvent action on the survival of mites

| Solvents | Average life time of Acaro (mites) in the solvents (Hours) | Standard Deviation | N |
|---|---|---|---|
| Isopropyl Myristate | 3.37 | 1.0294767 | 10 |
| Cetiol V | 8 | 0 | 10 |
| Cetiol HE | 0.08938 | 0.0126723 | 5 |
| Mineral Oil | 0.66412 | 0.3298975 | 5 |
| Absolute Ethanol | 0.03434 | 0.0092846 | 5 |

N: Number of mites in test

To prepare compositions, decyl oleate solvent (Cetiol V) was selected due to its excellent wetting properties on the skin. The Cetiol V is used in the preparation of water in oil emulsions or oil in water emulsions as the oil and is a good solvent of liposoluble active ingredients. Also, it has good flow properties, good penetrating power, and it facilitates entry through the epidermis.

TABLE NO. 3

Miscibility of oils in solvents

|  | Parts by volume v/v | Isopropy Myristate | Cetiol V | Cetiol HE |
|---|---|---|---|---|
| *Galanga* | 1/2 | YES | YES | YES |
|  | 1/10 | YES | YES | YES |
|  | 1/100 | YES | YES | YES |
|  | 1/1000 | YES | YES | YES |
| *Zingiber officinale* | 1/2 | YES | YES | NO |
|  | 1/10 | YES | YES | NO |
|  | 1/100 | YES | YES | NO |
|  | 1/1000 | YES | YES | NO |
| Tree Tea | 1/2 | YES | YES | YES |
|  | 1/10 | YES | YES | YES |
|  | 1/100 | YES | YES | YES |
|  | 1/1000 | YES | YES | YES |
| Black Pepper | 1/2 | YES | YES | NO |
|  | 1/10 | YES | YES | NO |
|  | 1/100 | YES | YES | NO |
|  | 1/1000 | YES | YES | NO |
| *Alpinia officinarum* | 1/2 | YES | YES | NO |
|  | 1/10 | YES | YES | NO |
|  | 1/100 | YES | YES | NO |
|  | 1/1000 | YES | YES | NO |
| *Eruca sativa* mili | 1/2 | ND | ND | ND |
|  | 1/10 | ND | YES | ND |
|  | 1/100 | ND | YES | ND |
|  | 1/1000 | ND | YES | ND |

ND: no determinado
YES: Miscibilidad completa < 1 min
NO: Miscibilidad incompleta > 1 min In Table 4 there is shown results of another the study of the present invention, using concentrations of 100%, 90%, 50% 25%, 12.5%, 1%, 0.5% and 0.25% dilution of Cetiol V for *Alpinia officinarum* oil and its acaricidal effect.

TABLE NO. 4

Evaluation acaricidal oil from *Alpinia officinarum* on *Demodex* Spp at different dilutions with Cetiol V

|  | Dilution | Number of mites evaluated | Average lifetime of the mite | Median | Trend | Standard Deviation | Variance | Minimum time of death of the mite | Maximum time of death of the mite |
|---|---|---|---|---|---|---|---|---|---|
| *Alpinia officinarum* | 100% | 10 | 3.95 | 4.02 | 4 | 0.27183 | 0.074 | 3.45 | 4.2 |
|  | 90.00% | 11 | 4.0136 | 4 | 4 | 0.17043 | 0.029 | 3.75 | 4.35 |
|  | 50.00% | 10 | 4.17 | 4.2 | 4.3 | 0.14181 | 0.02 | 3.9 | 4.3 |
|  | 25.00% | 10 | 7.855 | 7.65 | 7.3 | 1.09429 | 1.197 | 6.3 | 9.45 |
|  | 12.50% | 13 | 8.7962 | 9 | 10 | 1.8691 | 3.494 | 6 | 13 |
|  | 1% | 17 | 13.3529 | 14 | 14 | 0.93148 | 0.868 | 12 | 15 |
|  | 0.50% | 18 | 17.3333 | 17 | 16 | 2.0292 | 4.118 | 14 | 21 |
|  | 0.25% | 41 | 20.6544 | 21 | 28 | 6.5245 | 42.569 | 9.38 | 29 |

Table 5 below shows dilution of *Eruca sativa mili* essential oil with the diluent Cetiol V in various ranges of 100%, 90%, 50% 25%, 12.5%, 1%, 0.5% and 0.25% and the acaricidal effect.

TABLE NO. 5

Evaluation of Dilution of *Eruca sativa mili* essential oil with Cetiol V

| | Dilution | Number of mites evaluated | Average lifetime of the mite | Median | Trend | Standard Deviation | Variance | Minimum time of death of the mite. | Maximum time of death of the mite |
|---|---|---|---|---|---|---|---|---|---|
| Eruca sativa mili | 100% | 10 | 11.45 | 11.5 | 11 | 1.31581 | 1.731 | 9 | 13 |
| | 90.00% | 10 | 11.2600 | 11.0000 | 11 | .96056 | .923 | 10.00 | 13.00 |
| | 50.00% | 10 | 9.2170 | 9.5100 | 8.3 | 1.36074 | 1.852 | 7.10 | 11.00 |
| | 25.00% | 10 | 11.5810 | 11.3700 | 11.2 | 1.08005 | 1.166 | 10.00 | 14.25 |
| | 12.5% | 10 | 11.0990 | 11.0000 | 10.2 | .99169 | .983 | 10.20 | 13.20 |
| | 1% | 17 | 14.3041 | 15 | 15 | 0.92787 | 0.861 | 13 | 15.5 |
| | 0.50% | 43 | 18.5116 | 18 | 17 | 2.17532 | 4.732 | 15 | 24 |
| | 0.25% | 19 | 23.3363 | 24 | 24 | 1.37057 | 1.878 | 20 | 25 |

According to table 6 below, there is shown dilution of *Zingiber officinale* oil with the diluent Cetiol V in various ranges of 100%, 90%, 50% 25%, 12.5%, 1%, 0.5% and 0.25% and the acaricidal effect.

TABLE 6

Results acaricide activity of essential oils *Zingiber officinale* at different dilutions

| | Dilution | Number of mites evaluated | Average lifetime of the mite | Median | Trend | Standard Deviation | Variance | Minimum time of death of the mite. | Maximum time of death of the mite |
|---|---|---|---|---|---|---|---|---|---|
| Zingiber officinale | 100% | ND | ND | ND | ND | ND | ND | ND | ND |
| | 90.00% | ND | ND | ND | ND | ND | ND | ND | ND |
| | 50.00% | ND | ND | ND | ND | ND | ND | ND | ND |
| | 25.00% | ND | ND | ND | ND | ND | ND | ND | ND |
| | 12.5% | ND | ND | ND | ND | ND | ND | ND | ND* |
| | 1% | 20 | 18.8 | 19 | 17 | 1.50787 | 2.274 | 17 | 22 |
| | 0.50% | 21 | 39.8229 | 40.28 | 42 | 4.54292 | 20.638 | 30 | 53 |
| | 0.25% | 17 | 57.0588 | 57 | 56 | 1.74895 | 3.059 | 53 | 59 |

*Not determined because defined by the prior oils.

From the studies described in the tables above, it is clearly established that the percentage of effective dilution according to the present invention comprises between 50% and 0.25% for each essential oil.

Having established a working range for the effective amounts, the studies based herein show the most suitable percentages for each of the essential oils derived from each plant and their effect as an acaricide.

For the purpose of the invention, Table 7 describes several experimental evaluations of the acaricidal effect of the essential oils (death within minutes from the application to the mites) as defined by several fields of observation at different concentrations for each essential oil obtained from each plant. The concentration refers to the dilution of the oil from a 100% pure amount (pure essential oil obtained by reference). The dilution that was made, under the preferred embodiment according to the present invention was validated by studying the acaricidal effect in vivo through a clinical trial on the diluent. The Decyl Oleate (Cetiol V) diluent did not have acaricidal activity within 8 hours.

TABLE NO. 7

Results acaricidal activity of the three diluted essential oils

|  | Dilution | Number of sets analyzed | Number of mites evaluated | Average lifetime of the mite | Median | Trend | Standard Deviation | Variance | Minimum time of death of the mite. | Maximum time of death of the mite |
|---|---|---|---|---|---|---|---|---|---|---|
| *Eruca* | 12.5% | 5 | 10 | 11.0990 | 11.0000 | 10.2 | 0.99169 | 0.983 | 10.20 | 13.20 |
| *saliva* mili | 1% | 5 | 17 | 14.3600 | 14.33 | 13.83 | 0.53122 | 0.28200 | 13.83 | 15.11 |
|  | 0.25% | 5 | 19 | 23.4000 | 23.64 | 21.75 | 1.11020 | 1.23 | 21.75 | 24.66 |
| *Alpinia* | 12.5% | 5 | 13 | 8.7962 | 9 | 10 | 1.86910 | 3.494 | 6.00 | 13.00 |
| *officinarum* | 1% | 5 | 17 | 13.4160 | 13.33 | 14 | .57143 | 0.57 | 12.75 | 14.00 |
|  | 0.25% | 8 | 41 | 20.7863 | 21.77 | 9.61 | 6.73591 | 45 | 9.61 | 27.68 |
| *Zingiber* | 1% | 5 | 20 | 18.7360 | 18.6 | 17.33 | .95694 | 0.916 | 17.33 | 19.75 |
| *officinale* | 0.50% | 5 | 21 | 39.9040 | 40.6000 | 37.27 | 1.75961 | 3.096 | 37.27 | 41.66 |
|  | 0.25% | 5 | 17 | 56.9840 | 57.6 | 54.33 | 1.50267 | 2.28 | 54.33 | 58.00 |

The study described above established the effective concentration levels for each plant oil and based on those results, we proceeded to study and evaluate the acaricidal action of a combination preparation of essential oil blends of *Alpinia officinarum*, *Eruca sativa mili* and *Zingiber officinale* according to the present invention. To make the combined blend preparations, as reported above, decyl oleate (Cetiol V) solvent was used, because of its excellent wetting properties on the skin. It is also excellent for making oil in water and water in oil emulsions. Cetiol V is a good solvent for liposoluble active principles, it has good fluidity and penetrating power, and it also facilitates entry through the epidermis.

Other diluents also suggested for the composition of the present invention include PEG-7 Glycerol Cocoate (Cetiol HE), isopropyl myristate, isopropyl alcohol and absolute ethanol or combinations thereof.

According to the present invention, Cetiol V is especially suitable for combination with the essential oils of *Alpinia officinarum*, *Eruca sativa mili* and *Zingiber officinale* due to its compatibility for use on the skin and is fully compatible with skin fats without causing any irritation. According to the present invention, Cetiol V is incorporated into the fat phase of emulsions.

So, according to another object of the present invention, we proceeded to establish a combination of essential oils of these plants at different required concentrations based on the results of acaricidal action of each separately based on the tables above. This is evident in Table 8 below with *Eruca sativa milli* combined concentrations of between 12.5% and 0.25%; *Alpinia officinarum* between 12.5% and 0.25% and *Zingiber officinale* between 1% and 0.25%.

TABLE NO. 8

Cetiol V is incorporated into the emulsions in the oil phase

| Concentration | Initial Vol. (ul) | final volume (ul) | Time to death (min) |
|---|---|---|---|
| *Eruca sativa* mili 12.5%-0.25% | 5 | 1000 | 19 |
| *Alpinia officinarum* 12.5%-0.5% | 2.5 |  | 18 |
| *Zingiber officinale* 1%-0.25% | 10 |  | 19 |

For the above proposed combinations according to the present invention, efficacy in acaricidal action was found given the effective concentrations. The time of death of mites per field of observation (CO) is shown in Table 9 and in the last row the average of each field is defined for CO.

TABLE NO. 9

DMX Mixture (min)

| CO1 | CO2 | CO3 | CO4 | CO5 | CO6 | CO7 | CO8 | CO9 | CO10 | CO11 | CO12 | CO13 | CO14 | CO15 |
|---|---|---|---|---|---|---|---|---|---|---|---|---|---|---|
| 26 | 20 | 28 | 17 | 28 | 27 | 17 | 22 | 21 | 23 | 28 | 26 | 31 | 23 | 18 |
| 27 | 24 | 28 | 19 | 28 | 26 | 17 | 23 | 22 | 24 | 28 | 22 | 25 | 24 | 19 |
| 21 | 30 | 29 | 20 | 29 | 28 | 18 | 22 | 16 | 25 | 28 | 23 | 26 | 24 | 20 |
| 22 | 22 | 30 | 21 | 23 | 32 | 21 | 23 | 34 | 23 | 28 | 22 | 27 | 23 | 17 |
| 18 | 24 | 32 | 17 | 24 | 33 | 18 | 22 | 33 | 24 | 33 | — | — | 24 | — |
| — | — | 27 | 18 | — | — | 17 | 22 | — | — | — | — | — | 23 | — |
| 22.8 | 24 | 29 | 18.66 | 26.4 | 29.2 | 18 | 22.33 | 25.2 | 23.8 | 29 | 22.4 | 27.25 | 23.5 | 17.5 |

In conclusion and based on the studies discussed above, according to the present invention, an effective miticidal composition comprising a combination of essential oils of *Eruca sativa mili* at a dilution up to 99% is provided, preferably in an amount of 50% to 0.25% and more preferably between 12.5% and 0.25% *Eruca sativa mili* essential oil. The *Alpinia officinarum* is present in the composition, diluted in a proportion up to 99% and preferably up to 25% and more preferably between 12.5% and 0.25% of the *Alpinia officinarum* oil. The oil *Zingiber officinale*, is diluted in a ratio up to 99%, preferably up to 25% and more preferably between 1% and 0.25%. This combination of essential oils, then comprises the effective active blend having acaricidal action.

As illustrated in the photographic sequence of FIG. 1, the composition once it is delivered to the patient, their acaricidal activity starts with dehydration of the mite eggs by lipolytic effect that solubilizes the lipid membranes of the anatomical structure of the animal and therefore the consequent total elimination of the mite, forty minutes elapsed applied.

Meanwhile, then the acceptable for dilution of the essential oil solvent is selected from the group consisting of mineral oil, olive oil, Cetiol V, isopropyl myristate, Cetiol HE, alcohols and mixtures thereof. Also, as above, the preferred solvent for such dilution is decyl oleate.

Among the selected alcohols, they may be chosen from the group consisting of PEG-7, Glycerol Cocoate, (Cetiol HE), isopropyl myristate, isopropyl alcohol and absolute ethanol or combinations thereof.

Having determined as shown above the effective dilution for each essential oil, acaricides whose characteristics are the most effective, we also provide compositions for topical use.

One embodiment of the embodiments of the invention are compositions which comprise aqueous liquid solutions for ophthalmological use including extracts of essential oils of high quality in a precise relationship between them, said acaricidal compositions being 100% affective against *Demodex* ssp infestation. The pharmaceutical preparations or liquid forms according to the present invention comprises dosage forms such as solutions, emulsions and suspensions, among others.

Other therapeutic suitable delivery means according to the present invention without limiting the scope of the invention include powders, granules, capsules and tableting among others. Similarly, preparations or semisolid drug forms, for the present invention include ointments, creams and gels, among others.

Extracts of the essential oils of the invention are incorporated either in a liquid matrix compatible for use on the skin and eyes.

According to the present invention, particularly the composition comprises a proportion of *Eruca sativa milli* essential oil from 12.5 and 0.25%; a proportion of essential oil of *Alpinia officinarum* between 12.5 and 0.25%; a proportion of essential oil of *Zingiber officinale* between 1 and 0.25%; in combination with an pharmaceutically acceptable carrier.

Examples of delivery methods and physical forms include solutions, suspensions, aerosols, lotions, gels, pastes, impregnated wipes, impregnated tissue, impregnated non-woven substrates, medicinal balsams, cleaning products (including shampoos and soaps), creams or ointments, or a phytocosmetics composition in an preferred embodiment.

The composition of the present invention comprises in combination the essential oils of *Eruca sativa mili, Genjibre* and *Zingiber officinale*, water and at least pharmaceutically acceptable carrier; and at least one stabilizing agent and at least one excipient. It may also include consistency agents that impart texture and body to the final gel, and other optional components such as antioxidants, defoamers and flavoring.

So, under the preferred combination, the composition of the present invention provides an effective acaricide for eliminating 100% of the *Demodex* spp mite and their eggs, which causes Demodicosis and some forms of related diseases and rosacea.

According to the discussion above, in the prior art ophthalmic compositions are disclosed comprising natural oils such as tea tree oil and oils of the plants of the genus *Rhamnaceae*. However, in the disclosed prior art, the compositions of the invention including the oil (*Eruca sativa*), essential oil of *Alpinia officinarum* (*Alpinia officinarum*) or essential oil *Zingiber officinale Alpinia* galanga) are silent. The prior art does not specifically mention the inclusion of these three essential oils individually or in combination in a composition, which compositions facilitate comprehensive and efficient control of infection by *Demodex* and which in turn does not cause eye irritation.

So, the present invention comprises an acaricidal composition for the treatment of infections and diseases caused by the mite *Demodex* Spp, including essential oils selected from the group consisting of oil *Eruca sativa mili* oil, *Zingiber officinale* oil and *Alpinia officinarum* oil which essential oils are diluted in an acceptable solvent to form a composition as a solution, suspension, emulsion or dispersion.

The present invention comprises the use of a composition for the treatment of infections and diseases in humans caused by *Demodex* Spp, and the method of treatment of diseases in humans comprising solid forms, semisolid and liquid as liquid solutions emulsion, ointment, solution, lotion, shampoo, soap, foam and powder compact among others.

The present invention also relates to a kit for the treatment of diseases caused by the human *Demodex* Spp mite consists of:

(A) a composition comprising essential oils selected from the group consisting of *Eruca sativa* oil *mili* oil, *Zingiber officinale* and *Alpinia officinarum* oil; where essential oils are incorporated in an acceptable solvent; forming a solid or liquid dosage form, semisolid;

(B) an insert specifying the use of said composition to the affected area and the frequency of application; Y, and (C) an appropriate container for application of the dosage forms described.

The composition of the present invention, while comprising the combination of essential oils, whose therapeutic properties have been extensively studied over other microorganisms other than *Demodex* spp, necessarily incorporates these three oils into a single formulation, which is not specifically disclosed in the prior art. The composition of the present invention achieves greater efficiency and improved action of each of the three essential oils and they are incorporated at specific concentrations and in defined proportions, which is not specifically disclosed in the prior art. Additionally, the composition of the present invention is highly specific and of proven efficacy against mites.

The contents of all references cited in the instant specification and all cited references in each of those references are incorporated in their entirety by reference herein as if each of those references were individually denoted in the text.

Although the foregoing description (Angres) contains many specifics, these should not be construed as limiting the scope of the present invention, but merely as providing illustrations of some of the presently preferred embodiments. Similarly, other embodiments may be devised without departing from the spirit or scope of the present invention. Features from different embodiments may be employed in combination. The scope of the invention is, therefore, indicated and limited only by the appended claims and their legal equivalents rather than by the foregoing description. All additions, deletions and modifications to the invention as disclosed herein which fall within the meaning and scope of the claims are to be embraced thereby.

What is claimed is:

1. An acaricidal composition for the treatment of infections and diseases caused by a mite that is a species of *Demodex*, which comprises a mixture of essential oils, wherein the oils are *Eruca sativa* mill oil, *Zingiber officinale* oil and *Alpinia officinarum* oil.

2. The composition according to claim 1, wherein the essential oils are incorporated in an acceptable solvent.

3. The composition according to claim 2, wherein the acceptable solvent is selected from the group consisting of: mineral oils, olive oil, decyl oleate, isopropyl myristate, polyoxyethylene glyceryl monococoate, alcohols and mixtures thereof.

4. The composition according to claim 1, further comprising a pharmaceutically acceptable carrier.

5. The composition according to claim 3, wherein the composition is a solution, suspension, emulsion or dispersion.

6. A method of treating a disease in a human caused by a species of *Demodex*, said method comprising applying topically on the human a therapeutically effective amount of the composition of claim 1.

7. A Kit for the treatment of illnesses in humans that are caused by a mite that is a species of *Demodex* comprising:
  (A) the composition of claim 1, wherein the essential oils are incorporated into an acceptable solvent; and wherein the composition is a pharmaceutical solid, semisolid or liquid;
  (B) an insert specifying applying said composition to the affected area and the frequency of application; and
  (C) an appropriate container for the dosage forms.

8. The composition of claim 1, wherein the composition is formulated for topical application.

* * * * *